United States Patent [19]

Schabron

[11] Patent Number: 5,561,065

[45] Date of Patent: Oct. 1, 1996

[54] METHOD FOR TESTING EARTH SAMPLES FOR CONTAMINATION BY ORGANIC CONTAMINANTS

[75] Inventor: John F. Schabron, Laramie, Wyo.

[73] Assignee: University of Wyoming Research Corporation, Laramie, Wyo.

[21] Appl. No.: 337,897

[22] Filed: Nov. 14, 1994

[51] Int. Cl.$^6$ .................................................. G01N 33/24
[52] U.S. Cl. .............................. 436/28; 436/31; 436/139; 436/175; 422/61
[58] Field of Search ............................ 436/28–31, 32, 436/175, 164, 139; 422/61

[56] References Cited

U.S. PATENT DOCUMENTS

| | | | |
|---|---|---|---|
| 2,451,883 | 10/1948 | Squires | 250/71 |
| 3,149,068 | 9/1964 | Biederman, Jr. et al. | 210/31 |
| 4,992,379 | 2/1991 | Hanby | 436/29 |
| 5,050,425 | 9/1991 | Robbins | 73/19.1 |
| 5,140,845 | 8/1992 | Robbins | 73/19.03 |
| 5,181,428 | 1/1993 | Chriswell | 436/31 |
| 5,344,781 | 9/1994 | Kitchen et al. | 436/31 |

OTHER PUBLICATIONS

"Petroleum Hydrocarbons, Total Recoverable," Method 418.1 (Spectrophotometric, Infrared), Storet No. 45501, U.S. Environmental Protection Agency, pp. 418.1–1 through 418.1–3 (1978).

Grant, M., "TPH Field Screening Methodology Using Portable Infrared Instrumentation: A Case Study", Seventh Annual Conference on Hydrocarbon Contaminated Soils; University of Massachusetts, Amherst, Massachusetts, pp. 1–7 (1992).

"Fast, Low Cost Water and Soil Analysis", Advertising Literature, Hu–Hanby, 7 pages, date unknown.

"Announcing the Horiba Instruments, T.P.H. (Total Petroleum Hydrocarbon) Soil Analysis Products," Advertising literature, Horiba, 6 pages, date unknown.

"Petro–Flag™ Hydrocarbon Test Kit," Dexsil Corporation, one page (1994).

"Envirolert 5100 On–Line Oil–in Water Monitor," Advertising Literature, Invalco, 4 pages, date unknown.

"Water Quality Instrumentation," Advertising Literature, Phox Systems Ltd., 4 pages, date unknown.

Saenz, G. et al., "A Method of soil Analysis to Detect and Delinerate Subsurface Hydrocarbon Contaminants by Means of Aromatic Hydrocarbons," 1991 Proc. Petroleum Hydrocarbon and Organic Chemicals in Groundwater; Prevention, Detection, and Restoration, Houston, Texas Assoc. of Groundwater Scientists and Engineers and American Petroleum Institute, pp. 59–72.

Driscoll, J., "Hydrocarbon Screening Methods," Environmental Testing and Analysis, pp. 23–27 (Jan./Feb. 1993).

(List continued on next page.)

Primary Examiner—Lyle A. Alexander
Attorney, Agent, or Firm—Sheridan Ross & McIntosh

[57] ABSTRACT

Provided is a method for testing earth samples for contamination by organic contaminants, and particularly for aromatic compounds such as those found in diesel fuel and other heavy fuel oils, kerosene, creosote, coal oil, tars and asphalts. A drying step is provided in which a drying agent is contacted with either the earth sample or a liquid extract phase to reduce to possibility of false indications of contamination that could occur when humic material is present in the earth sample. This is particularly a problem when using relatively safe, non-toxic and inexpensive polar solvents such as isopropyl alcohol since the humic material tends to be very soluble in those solvents when water is present. Also provided is an ultraviolet spectroscopic measuring technique for obtaining an indication as to whether a liquid extract phase contains aromatic organic contaminants. In one embodiment, the liquid extract phase is subjected to a narrow and discrete band of radiation including a desired wave length and the ability of the liquid extract phase to absorb that wavelength of ultraviolet radiation is measured to provide an indication of the presence of aromatic organic contaminants.

22 Claims, 2 Drawing Sheets

OTHER PUBLICATIONS

Michelson, T., et al., "Cleanup Standards for Petroleum Hydrocarbons. Part 1. Review of Methods and Recent Developments," Journal of Soil Contamination, 2(2), pp. 109–124 (1993).

Simmons, K., "A Real–Time TPH Field Analysis Method," On Site Analysis, American Environmental Laboratory, pp. 1, 28 (Jun. 1993).

"Total Petroleum Hydrocarbon (TPH) Measurements at Utility Sites," Land and Water Quality News, vol. 7, No. 1, pp. 21–23 (Apr. 1994).

Manke, E., et al., "Screening Around Tanks: Choose the Right Method," Soils, pp. 40–43 (Jun./Jul. 1993).

"Field–Portable Scanning Spectrofluorometer," U.S. Environmental Protection Agency, Environmental Systems Monitoring Laboratory, Las Vegas, Nevada, 4 pages (Jun. 1993).

Poziomek, E., "Solid–Phase Extraction and Solid–State Spectroscopy For Monitoring Water Pollution," Analytical Letters, 24(10), Marcel Dekker, Inc., pp. 1913–1921 (1991).

"Standard Test Method for Quantification of Complex Polycyclic Aromatic Mixtures or Petroleum Oils in Water," ASTM Draft No. 11, pp. 1–39 (Jun. 1992).

METHOD FOR TESTING EARTH SAMPLES FOR CONTAMINATION BY ORGANIC CONTAMINANTS

ACKNOWLEDGEMENT OF GOVERNMENT SUPPORT

This invention was made with Government support under Cooperative Agreement Number DE-FC21-93MC30127 awarded by the Department of Energy. The Government has certain rights in this invention.

FIELD OF THE INVENTION

The present invention involves a method for testing earth samples for the presence of possible organic contaminants, and particularly for the presence of aromatic compounds.

BACKGROUND OF THE INVENTION

Contamination of the earth by organic contaminants is a major concern due to the possible environmental, health and financial problems relating to such contamination. Possible contaminants include a variety of organic materials such as crude petroleum, fossil fuels, lubricating oils and greases, solvents and others. It is economically and socially desirable to be able to identify contaminated sites so that potential risks can be evaluated and remedial action can be properly planned and pursued.

Sophisticated laboratory techniques are available to measure the presence and level of contaminants in earth samples. One such technique is to evaluate contaminants using chromatography. Sophisticated laboratory techniques, however, are expensive and are, therefore, typically impractical for use in large site surveys that require many tests to be performed in a systematic manner. They are also not well suited for use in the field. It is, therefore, desirable to have a testing technique which could be easily and inexpensively used in the field to identify contaminated sites. Once identified, then more elaborate laboratory tests could be performed to identify specific contaminants and to assist in planning for remediation, if necessary.

Several field testing techniques have been proposed in which a soil sample is extracted with a solvent to remove organic contaminants. The extract phase is then analyzed to gain information concerning the presence of contaminants and/or the level of contamination. One technique that has been used extensively for field testing involves the use of infrared spectroscopy to measure carbon-hydrogen bond stretch and uses a chlorofluorocarbon solvent. Chlorofluorocarbon solvents, however, pose serious environmental problems and their use is being severely restricted. Another technique involves indirect measurement for the presence of contaminants by looking for a color change in the extract phase caused by the presence of a Friedel-Crafts reaction in the presence of a Friedel-Crafts catalyst. That technique, however, uses an alkyl halide as a solvent, such as carbon tetrachloride, a known carcinogen. This technique, therefore, involves a serious health hazard. To reduce environmental and health risks, it would be desirable to avoid the use of halogenated organic solvents such as chlorofluorocarbons and carbon tetrachloride.

One technique that has been proposed involves an immunoassay and uses methanol as a solvent. The presence of contaminants is measured indirectly in an extract phase by observing color changes related to the activity of a biological agent that is added to the extract phase. Like the method using a Friedel-Crafts reaction, however, the immunoassay technique provides only an indirect indication of the presence of contaminants. The use of an indirect measurement, however, complicates testing and provides an additional opportunity for making a measurement error. Additionally, because of the use of a biological agent, the immunoassay technique is useful only over a narrow temperature range and the test kits have a very short shelf life. These limitations seriously limit the utility of the immunoassay technique in many field operations.

Based on the significant economic, health and environmental interests in identifying contaminated sites, it would be advantageous to provide a field testing procedure that is relatively inexpensive, reliable and safe and that is well suited for the variety of conditions that may be experienced during field testing.

SUMMARY OF THE INVENTION

The present invention provides a relatively inexpensive, safe and effective method for testing earth samples for the presence of organic contaminants, and especially for the presence of aromatic compounds such as those found in diesel fuel and other heavy fuel oils, kerosene, creosote, coal oil, tars, and asphalts. An earth sample is extracted with a solvent to remove possible organic contaminants from the earth sample. A liquid extract phase from the extraction can then be analyzed to identify the presence of possible organic contaminants.

In one aspect, the present invention permits the use of relatively safe, non-toxic and inexpensive polar organic solvents to extract earth samples to test for contamination by organic contaminants. Lower alcohols, and particularly isopropyl alcohol, are preferred due to their relatively safe and non-toxic nature and their relatively low cost. Lower alcohols are also very versatile in that they dissolve a variety of organic contaminants and can be used over a wide temperature range. The problems associated with using halogenated solvents such as chlorofluorocarbons and carbon tetrachloride are avoided.

When an earth sample contains humic material, however, it is possible that a false indication of contamination could result, especially when using polar organic solvents such as lower alcohols because humic materials are often soluble in polar solvents, and especially when water is present. To reduce the possibility for false indications of contamination when humic material is present in an earth sample, the process of the present invention provides a drying step which can be performed on the earth sample or on the extract phase. The drying step is particularly useful when an earth sample is wet because humic material tends to extract into polar organic solvents along with water. A drying agent is added to the earth sample or to the liquid extract phase to tie up humic material and to reduce the ability of humic material to dissolve into the extract phase, or to remain dissolved in the extract phase. Preferred drying agents include compounds having an alkaline earth metal. Oxides of alkaline earth metals have been found to be particularly effective at reducing the ability of humic material to interfere with testing. Calcium oxide is especially preferred because it is very effective for tying up humic material and is easy to use in the field.

In one embodiment, the extract is measured for possible contamination by subjecting it to only a few, and preferably to only one, narrow and discrete bands of ultraviolet radiation. A response of the extract phase to each of the discrete and narrow bands is separately measured and evaluated to provide an indication of contamination. A preferred measurement evaluation involves determining absorption by the extract phase of a single wave length of ultraviolet radiation to provide an indication of contamination. The absorption measurement is extremely simple to perform in the field and can be done with simple, inexpensive equipment. The use of an expensive scanning spectrophotometer can be avoided because there is no need to scan and evaluate a wide spectrum of radiation wavelengths. Additionally, a measurement of a fluorescent emission could be made instead of or in addition to the absorption measurement.

The ultraviolet measurement technique of the present invention is particularly useful for identifying contamination by aromatic compounds. In many instances, however, it may be desirable to also test for non-aromatic organic contaminants, such as the lighter aliphatic hydrocarbons present in gasolines and the non-aromatic components in many industrial solvents, such as trichloroethane. In another embodiment, the present invention also provides that, in addition to the ultraviolet measurement for detecting aromatic compounds, sampling of a vapor space located adjacent to an earth sample can also be performed to provide an indication of possible contamination by volatile organic components, such as those that might be present in gasoline or in many industrial solvents.

DETAILED DESCRIPTION

Figure 1:
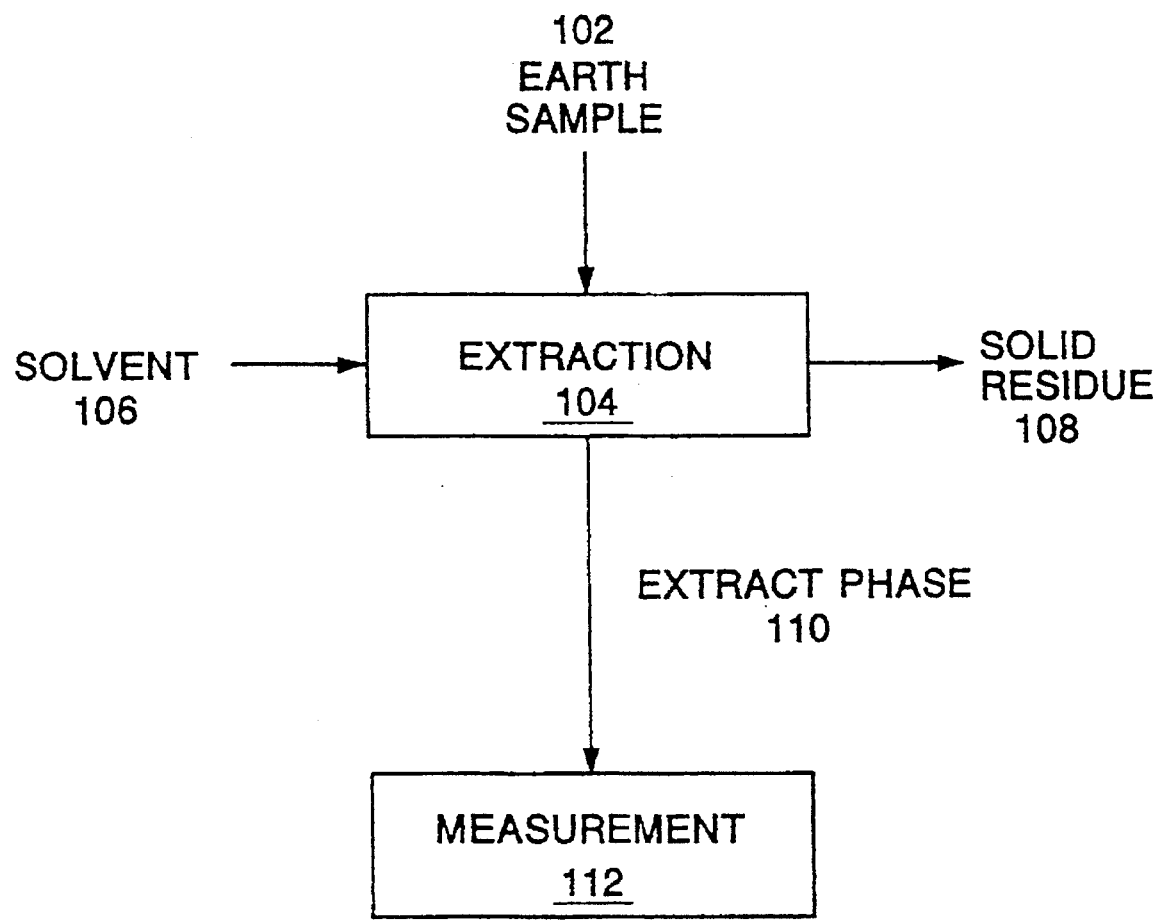
FIG. 1 shows a flow diagram of one embodiment of the process of the present invention.

The present invention provides a process for testing earth samples for the presence of organic contaminants. The process is especially useful for identifying aromatic compounds such as those found in diesel and other heavy fuel oils, kerosene, creosote, coal oil, tars and asphalts. The basic process flow is shown in FIG. 1. An earth sample 102 is provided for testing and is subjected to extraction 104, where a solvent 106 is contacted with the earth sample 102 to dissolve possible organic contaminants from the earth sample 102. The solvent 106 can be any suitable solvent, but polar solvents such as lower alcohols are preferred due to their versatility in functioning over a wide temperature range and their ability to dissolve a variety of organic contaminants. Isopropyl alcohol is particularly preferred, as discussed later. The liquid extract phase 110, comprising the solvent 106 and organic contaminants that may have been extracted from the earth sample 102, is separated from the solid residue 108 for measurement 112 to identify the presence of possible organic contaminants. The solid residue 108 of the earth sample following extraction 104 is generally disposed of as waste.

Extraction 104 can be performed in the field by mixing the earth sample with the solvent in a suitable container, such as a mason jar. The earth sample 102 and the solvent 104 should be thoroughly mixed to assure good contact between the solvent 106 and the earth sample 102. Use of a mechanical mixer is preferred. The solid residue 108 can be separated from the extract phase by any solid/liquid separation technique. One separation method is to use a filter, such as a syringe filter, on which the solid residue will be retained and through which the extract phase 110 will pass as filtrate.

During the measurement 112, the liquid extract phase 110 is analyzed for the presence of organic contaminants that may have been extracted from the earth sample 102. Although any analysis technique may be used, the measurement 112 typically involves a spectroscopic measurement to provide a direct measurement of the presence of organic contaminants. The problems associated with indirect measurement techniques are thereby avoided.

Problems during the measurement 112 can occur, however, when the earth sample being tested contains humic material. It is possible that humic material in an earth sample can be extracted into the solvent during the extraction 104 and can provide a false indication of contamination during the measurement 112, especially when the measurement 112 includes an ultraviolet spectroscopic measurement technique as discussed below. The potential for a false indication of contamination is especially large when using a polar solvent, such as isopropyl alcohol, because humic material is generally highly soluble in polar solvents and may be readily extracted from the earth sample 102, especially if water is present in the earth sample 102. As used herein, humic material refers to naturally occurring organic material in soils from the decay of leaves, wood and other vegetable matter. Humic material may contain, for example, humic acid, fulvic acid and/or humin.

Figure 2:
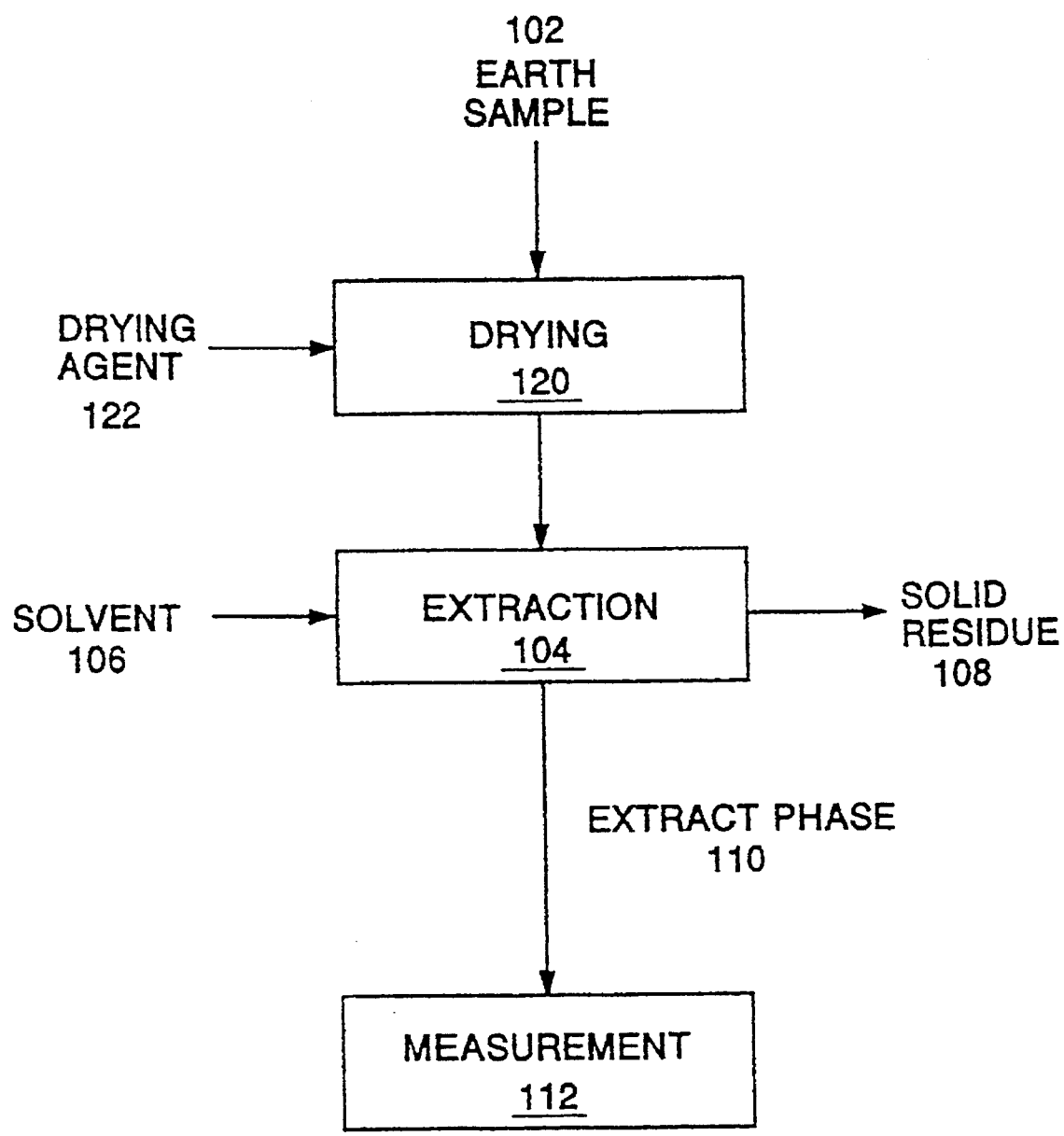
FIG. 2 shows a flow diagram of another embodiment of the process of the present invention.

It has been found that a drying step can be used to reduce the possibility of a false indication of contamination when humic material is present in the earth sample 102. FIG. 2 shows a process flow diagram for one embodiment of the process of the present invention including such a drying step. Prior to extraction 104, the earth sample 102 is subjected to drying 120 in which a drying agent 122 is contacted with the earth sample 102. The drying agent dries water that may be present in the earth sample 102 and reduces the ability of humic materials in the earth sample to dissolve into the solvent 106 during the extraction 104. The possibility is, thereby, reduced that humic material will be present in the extract phase 110 and, accordingly, that a false indication of contamination will result during the measurement 112. Although it is preferred that the drying 120 precede the extraction 104, as shown in FIG. 2, the drying 120 could alternatively follow the extraction 104 and be performed directly on the extract phase 110. In that case, the extract phase 110 would be contacted with the drying agent 122 to dry water in the extract phase 110 and to tie up humic material so that it can be easily removed from the extract phase, such as by filtering. Although the drying 120 is not required when an earth sample contains no humic material, performing the drying step is always advisable as a safeguard measure.

Any additive can be used as the drying agent 122 which is capable of sufficiently reducing the ability of humic material to dissolve in, or to remain dissolved in, the solvent 106. Because humic material tends to extract from an earth sample with water, preferred additives are hygroscopic and are capable of tying up water and substantially preventing water from dissolving in, or remaining dissolved in, the solvent 106. One preferred class of additives includes compounds having a divalent cation, and especially a divalent cation of an alkaline earth metal. Oxides of alkaline earth metals are particularly preferred due to their high affinity for water and their ability to form relatively insoluble hydroxides. Although magnesium oxide and calcium oxide work well, calcium oxide is superior because it is easier to mix with the earth sample, especially when wet, without clumping that could complicate the drying 120 or the extraction 104.

The drying agent 122 should be added in an amount that is sufficient to dry substantially all of the water present in the earth sample 102. Usually, about one gram of the drying agent 122 per gram of the earth sample 102 should be sufficient for even very wet earth samples, but additional drying agent can be added, if desired. The drying 120 is easy to perform in the field. Simple mechanical stirring of the drying agent 122 and the earth sample 102 is sufficient for adequate contacting.

The solvent 106 that is used in the extraction step can be any solvent suitable for dissolving potential contaminants, but is preferably an organic solvent. For example, a low polarity hydrocarbon solvent such as n-heptane can be used. The solvent should be effective for dissolving aromatic compounds such as those associated with diesel fuel and other heavy fuel oils, kerosene, creosote, coal oil, tars or asphalts. These aromatic compounds include polyaromatic hydrocarbons, which are particularly suited for detection according to the process of the present invention.

Polar organic solvents which are capable of dissolving water work well because any water extracted during the extraction 104 will form a single phase with the solvent 106 in the extract phase 110 to permit easy measurement of the single phase during the measurement 112. It is not necessary to remove water from the extract phase. Oxygenated organic compounds, and particularly the lower alcohols, are preferred polar organic solvents. The lower alcohols (C1–C5 alcohols) are versatile because they can dissolve a variety of contaminants and can be used over a wide temperature range. The lower alcohols are relatively safe and easy to use, without significant risk of serious health or environmental hazards when properly used. Especially preferred among the lower alcohols is isopropyl alcohol which provides great flexibility and versatility at low cost and can be used safely and effectively in the field. Alternatively, a hydrocarbon solvent that does not absorb ultraviolet radiation can be used, such as h-heptane, providing that the earth sample 102 has been adequately dried.

The solvent 106 should be added in an amount sufficient to extract substantially all organic contaminants that may be in the earth sample 102. For isopropyl alcohol, about 10 milliliters of solvent 106 per gram of earth sample 102 is typically sufficient.

The measurement 112 to identify the presence of possible contaminants in the extract phase 110 can involve any appropriate measurement technique. In one aspect, however, the present invention provides a simple method for detecting the presence of aromatic contaminants, such as those found in diesel fuel and other heavy fuel oils, kerosene, creosote, coal oil, tars and asphalts. To avoid the use of expensive scanning spectrophotometers, irradiation is performed only at a limited number of discrete wavelengths. The extract phase 110 is subjected to an ultraviolet radiation source and a response of the extract phase 110 to the ultraviolet radiation is evaluated. The number of discrete wavelengths to which the extract phase 110 is subjected should be no more than 10, and preferably three or fewer. It should be recognized that by a discrete wavelength, it is meant that the extract phase 110 is subjected to a very narrow band of ultraviolet radiation that includes the wavelength of interest. The desired wavelength should be in a narrow and discrete band of wavelengths that is narrower than 5 nanometers.

In one embodiment, a particularly simple but effective evaluation can be made by subjecting the extract phase 110 to a single discrete wavelength of ultraviolet radiation. A single wavelength is preferred because of simplicity. For example, the extract phase can be subjected to ultraviolet radiation at a wavelength of 254 nanometers in a spectrophotometer which can measure the amount of ultraviolet radiation of that wavelength that is absorbed by the extract phase 110. The absorption measurement provides a direct indication of the presence of aromatic organic contaminants in the extract phase. The absorption reading can be compared to the response of predetermined standard solutions to identify approximate levels of contamination. Due to the variation between the composition of various contaminants, including differences between individual diesel fuels, average absorptivities for a particular fuel type can be used for rough indications of contamination. If the source of contamination is known, however, then standard solutions can be prepared using the known source material to improve accuracy. As an example of the absorption measurement of the present invention, the extract phase 110 is subjected to ultraviolet radiation at a wavelength of 254 nanometers. Radiation from a source such as a mercury lamp could be filtered to provide a narrow band of radiation about the wavelength of interest to which the extract phase 110 is subjected. A photodiode for detecting the wavelength of interest could be used to measure radiation at 254 nanometers that passes through the extract phase, permitting a determination of absorption.

Although not as simple as an absorption measurement, a measurement for a fluorescent emission from the extract phase 110 in response to excitation by ultraviolet radiation could be made instead of the absorption measurement. A fluorescent emission indicates the presence of organic contaminants. For example, the extract phase 110 can be subjected to an excitation wavelength of 254 nanometers and an emission wavelength at 340 nanometers can be measured to provide an indication of the presence of organic contaminants. Again, the intensity of the fluorescent emission could be compared to previously prepared standard solutions to provide an indication of the level of contamination. Multiple excitation wavelengths could be used with multiple fluorescent emission measurements. For example, excitation wavelengths of 254 nanometers and 280 nanometers could be used with corresponding measurements of emission wavelengths at 340 nanometers and 450 nanometers. Preferably, however, no more than 10 discrete excitation wavelengths are used and no more than 10 discrete emission wavelengths are measured.

It is possible to combine in the measurement 112 both absorption information and fluorescent emission information. For example, absorption could be measured in line with the radiation source and fluorescent emission could be measured at a 90° angle to the radiation source. Various comparisons can be made between absorption and fluorescent emission measurements and between multiple fluorescent emission measurements to assist in fingerprinting the contaminants to assist in identifying the source of the contaminants, if desired.

As noted previously, when using an ultraviolet spectroscopic measurement technique, as described, whether involving measurement of absorption or fluorescent emission characteristics, there is a possibility of a false indication of contamination when the earth sample 102 contains humic material. Humic material can absorb ultraviolet radiation and can also fluoresce in response to ultraviolet radiation. Therefore, it is preferred that the drying 120 be used, as previously described. The combination of using the drying step to reduce problems that could occur when humic materials are present with the very simple ultraviolet spectroscopic measurement techniques, and particularly the absorption technique, provides a versatile and relatively low cost and safe process for testing earth samples for contaminants.

The ultraviolet measurement techniques of the present invention are well suited for identifying aromatic contaminants, as noted. Many organic contaminants, however, such as gasolines and many industrial organic solvents, contain few, if any, aromatic components. With the process of the present invention, however, it is possible to test for volatile, non-aromatic compounds that are typically present in gasolines and many industrial organic solvents, such as trichloroethylene, in addition to testing for aromatic contaminants as already described. Volatile organic components can be tested by sampling a vapor space adjacent to the earth sample 102, such as with a flame ionization detector or a photoionization detector, prior to the drying 120 or the extraction 104. For example, a lid to a mason jar could be fitted with a sampling port to permit sampling of the head space above the earth sample in the mason jar. The earth sample 102 could then be dried, extracted and measured, as previously described. Alternatively, a first portion of the earth sample 102 could be used to detect the presence of volatile organic components and a second portion of the earth sample 102 could be extracted for the measurement of aromatic contaminants, as previously described.

The present invention will now be further described by the following nonlimiting examples.

EXAMPLES 1-20

Examples 1–20 demonstrate that false indications of contamination that can be caused by the presence of humic material and the use of calcium oxide as a drying agent to reduce the possibility of a false indication of contamination.

Tests are performed on four different soils: a sandy soil, a silty soil, a clayey soil, and a commercially available potting soil which contains a significant amount of humic material. Two series of tests are run for each type of sample. In the first test series, the samples are blanks and contain no contaminants. In the second test series, the samples are spiked with a commercially available No. 2 diesel fuel to provide 400 milligrams of diesel per kilogram of soil. In each test series, five different test samples are prepared for each soil type, as follows: (1) a ten gram soil sample with no added water; (2) a ten gram soil sample mixed with 2.5 milliliters of water; (3) a ten gram soil sample mixed with 2.5 milliliters of water and dried with 5 grams of calcium oxide; (4) a ten gram soil sample mixed with 10 milliliters of water; and (5) a ten gram soil sample mixed with 10 milliliters of water and dried with 15 grams of calcium oxide.

For each test, the sample is extracted by placing the sample into a bottle and adding 100 milliliters of isopropyl alcohol as an extraction solvent. The sample and the extraction solvent are mixed with a magnetic stirrer for three minutes. The mixture is then allowed to settle and the supernatant solution is poured into a 10 milliliter syringe and is filtered through a 0.45 micron syringe filter. The filtrate is then placed in a Shimadzu Model UV-265 scanning spectrophotometer and the absorption of ultraviolet radiation at a wavelength of 254 nanometers is measured and compared with standard solution measurements previously made using various concentrations of the diesel fuel in isopropyl alcohol.

The results of Examples 1–20 are summarized in Table 1. Test results for the blank samples indicate that blank readings are generally acceptably low for the sandy, silty and clayey soils. The potting soil sample, however, having a significant amount of humic material, shows very high blank sample absorptions which, if not accounted for, would provide false indications of contamination. The blank readings are even higher in potting soil samples containing water, indicating that wet earth samples having humic material are particularly vulnerable to providing false indications of contamination. By adding calcium oxide, however, all of the blank absorption readings are reduced to an acceptably low level. The data for the spiked samples indicates that isopropyl alcohol is an effective solvent for extracting the diesel contaminants from the soil samples.

TABLE 1

| Example No. | Sample | Blank Sample (AU)[1] | Spiked Sample (% Recovery)[2] |
|---|---|---|---|
| 1 | Sand | <0.001 | 112 |
| 2 | Sand + 2.5 ml water | 0.020 | 80 |
| 3 | Sand + 2.5 ml water + 5 g CaO | <0.001 | 74 |
| 4 | Sand + 10 ml water | <0.001 | 111 |
| 5 | Sand + 10 ml water + 15 g CaO | <0.001 | 66 |
| 6 | Silt | <0.001 | 106 |
| 7 | Silt + 2.5 ml water | <0.001 | 96 |
| 8 | Silt + 2.5 ml water + 5 g CaO | <0.001 | 83 |
| 9 | Silt + 10 ml water | <0.001 | 87 |
| 10 | Silt + 10 ml water + 15 g CaO | 0.010 | 64 |
| 11 | Clay | 0.015 | 100 |
| 12 | Clay + 2.5 ml water | 0.038 | 103 |
| 13 | Clay + 2.5 ml water + 5 g CaO | <0.001 | 92 |
| 14 | Clay + 10 ml water | 0.038 | 97 |
| 15 | Clay + 10 ml water + 15 g CaO | 0.048, 0.025 | 94 |
| 16 | Potting soil | 0.060 | 100 |
| 17 | Potting soil + 2.5 ml water | 0.140 | 110 |
| 18 | Potting soil + 2.5 ml water + 5 g CaO | 0.018 | 92 |
| 19 | Potting soil + 10 ml water | 0.180 | 118 |
| 20 | Potting soil + 10 ml water + 15 g CaO | 0.075, 0.040 | 102 |

[1]Absorbance Units at 254 nm
[2]Percent of available diesel apparently extracted based on comparison of the absorption reading of the extract phase (corrected for the corresponding blank absorption reading) to standard solutions.

EXAMPLES 21-36

Examples 21–36 show the use of various drying agents to reduce problems that could be caused by the presence of humic material in a liquid extract phase.

A test solution is prepared containing 35 milligrams per liter of humic acid in distilled water. One 50 milliliter sample of the solution is subjected to ultraviolet radiation at 254 nanometers and absorption of the ultraviolet radiation at that wavelength is determined. To additional 50 milliliter samples are added 1 gram and 5 gram portions of various drying agents. These samples are filtered to remove solid particulates and the filtrate is subjected to ultraviolet radiation at 254 nanometers and absorption at that wavelength is determined.

The results of Examples 21–36 are shown in Table 2. The results indicate that the alkaline earth metal compositions are superior to alkali metal compositions. Calcium oxide, magnesium oxide and magnesium chloride provide the lowest absorption readings, indicating that they are particularly effective for preventing the humic acid from interfering with absorption measurements.

TABLE 2

| Example No. | Liquid Sample | Drying Agent | Absorption @ 254 nm (AU)[1] |
|---|---|---|---|
| 21 | Distilled Water | None | 0.00 |
| 22 | 35 mg/l Humic Acid | None | 0.98 |
| 23 | 35 mg/l Humic Acid | 1 g CaCl$_2$ | 0.22 |
| 24 | 35 mg/l Humic Acid | 5 g CaCl$_2$ | 0.31 |
| 25 | 35 mg/l Humic Acid | 1 g MgSO$_4$ | 0.55 |
| 26 | 35 mg/l Humic Acid | 5 g MgSO$_4$ | 0.57 |
| 27 | 35 mg/l Humic Acid | 1 g Na$_2$SO$_4$ | 0.88 |
| 28 | 35 mg/l Humic Acid | 5 g Na$_2$SO$_4$ | 0.84 |
| 29 | 35 mg/l Humic Acid | 1 g MgCl$_2$ | 0.02 |
| 30 | 35 mg/l Humic Acid | 5 g MgCl$_2$ | 0.05 |
| 31 | 35 mg/l Humic Acid | 1 g CaSO$_4$ | 0.12 |
| 32 | 35 mg/l Humic Acid | 5 g CaSO$_4$ | 0.12 |
| 33 | 35 mg/l Humic Acid | 1 g CaO | 0.04 |
| 34 | 35 mg/l Humic Acid | 5 g CaO | 0.03 |
| 35 | 35 mg/l Humic Acid | 1 g MgO | 0.04 |
| 36 | 35 mg/l Humic Acid | 5 g MgO | 0.00 |

[1]Absorbance Units

EXAMPLES 37–52

Examples 37–52 demonstrate the addition of various drying agents to earth samples made from potting soil, which contains a high level of humic material.

Samples are prepared containing 2.5 grams of potting soil and 2.5 milliliters of distilled water. Five grams of various drying agents are added to and thoroughly mixed with the samples. The mixture is then extracted by adding 50 milliliters of isopropyl alcohol to the mixture and stirring the mixture on a magnetic stirrer plate for three minutes. The extracted samples are then filtered and the filtrate from each test is subjected to ultraviolet radiation at 254 nanometers and absorption at 254 nanometers is determined. Two tests are run for each drying agent.

The results of Examples 37–52 are shown in Table 3 and indicate that the alkaline earth metal compounds perform superior to the alkali metal compounds. Also, calcium oxide and magnesium oxide appear to be superior to the other drying agents. Calcium oxide, however, is preferred over magnesium oxide because calcium oxide is easier to mix with the earth sample and stirs easily, unlike magnesium oxide and some of the other drying agents which tend to clump or form cement-like chunks which may interfere with testing operations.

TABLE 3

| Example No. | Sample[1] | Drying Agent[2] | Absorption @ 254 nm (AU)[3] | Comments |
|---|---|---|---|---|
| 37 | Potting Soil/Water | None | 0.341 | |
| 38 | Potting Soil/Water | None | 0.367 | |
| 39 | Potting Soil/Water | CaCl$_2$ | 0.086 | clumpy |
| 40 | Potting Soil/Water | CaCl$_2$ | 0.046 | clumpy |
| 41 | Potting Soil/Water | MgSO$_4$ | 0.036 | cement-like chunks |
| 42 | Potting Soil/Water | MgSO$_4$ | 0.007 | cement-like chunks |
| 43 | Potting Soil/Water | Na$_2$SO$_4$ | 0.284 | |
| 44 | Potting Soil/Water | Na$_2$SO$_4$ | 0.178 | |
| 45 | Potting Soil/Water | MgCl$_2$ | 0.326 | |
| 46 | Potting Soil/Water | MgCl$_2$ | 0.254 | |
| 47 | Potting Soil/Water | CaSO$_4$ | 0.124 | cement-like chunks |
| 48 | Potting Soil/Water | CaSO$_4$ | 0.083 | cement-like chunks |
| 49 | Potting Soil/Water | CaO | 0.026 | stirs well |
| 50 | Potting Soil/Water | CaO | 0.037 | stirs well |
| 51 | Potting Soil/Water | MgO | 0.113 | clumpy |
| 52 | Potting Soil/Water | MgO | 0.071 | clumpy |

[1]2.5 g potting soil and 2.5 ml water
[2]5 g portions of drying agent
[3]Absorbance Units Various embodiments of the present invention have been described in detail. It should be recognized that any elements of any of these described embodiments can be combined in any combination with elements of any other embodiment. For example, any combination of solvent, drying agent and measurement technique can be used. Furthermore, modifications and adaptations of the disclosed embodiments will be apparent to those skilled in the art. It is to be expressly understood that such modifications and adaptations are within the scope of the present invention as set forth in the following claims.

What is claimed is:

1. A method for testing an earth sample for the presence of a possible organic contaminants, and that reduces the risk of a false positive indication of contamination from humic material that is frequently present in earth samples, the method comprising the steps of:

providing an earth sample for testing for the presence of an organic contaminant;

providing an additive capable of interacting with and tying up water said additive comprising at least one of an alkaline earth metal salt and an alkaline earth metal oxide;

providing an organic solvent for use in extracting said earth sample, said organic solvent capable of dissolving said organic contaminant;

extracting said earth sample, comprising contacting said earth sample with said solvent to form a solid residue and a substantially liquid extract phase comprising said solvent;

measuring at least one property of said extract phase for an indication of whether said extract phase contains said organic contaminant, wherein said at least one property is selected from the group consisting of absorption by said extract phase of ultraviolet radiation, fluorescent emission from said extract phase and combinations thereof, treating, prior to said measuring step, at least one of said earth sample and said extract phase with said additive to reduce the possibility, during said measuring step, of a false positive indication of the presence of said organic contaminant that could occur when humic material is present in said earth sample.

2. The method of claim 1 for testing an earth sample, wherein:

said step of treating comprises contacting said earth sample with said additive prior to said step of extracting said earth sample.

3. The method of claim 1 for testing an earth sample, wherein:

said step of treating comprises contacting, prior to said step of extracting, said earth sample with said additive to tie up water present in said earth sample and thereby prevent at least some of said water from dissolving into said solvent during said extracting step.

4. The method of claim 1 for testing an earth sample wherein:

said additive comprises a hygroscopic material.

5. The method of claim 1 for testing an earth sample, wherein:

said additive comprises an oxide of an alkaline earth metal.

6. The method of claim 1 for testing an earth sample, wherein:

said additive comprises calcium.

7. The method of claim 1 for testing an earth sample, wherein:

said additive comprises calcium oxide.

8. The method of claim 1 for testing an earth sample, wherein:

said solvent comprises a non-halogenated organic compound.

9. The method of claim 1 for testing an earth sample, wherein:

said solvent comprises a polar organic compound in which water is soluble.

10. The method of claim 1 for testing an earth sample, wherein:

said solvent comprises an oxygenated organic compound.

11. The method of claim 1 for testing an earth sample, wherein:

said solvent comprises an alcohol.

12. The method of claim 1 for testing an earth sample, wherein:

said solvent comprises isopropyl alcohol.

13. The method of claim 1 for testing an earth sample, wherein:

said step of measuring at least one property of said extract phase comprises determining the ability of said extract phase to absorb ultraviolet radiation to provide an indication of possible contamination by aromatic compounds.

14. The method of claim 1 for testing an earth sample, wherein:

said step of measuring at least one property of said extract phase comprises measuring for the presence of a fluorescent emission from said extract phase to provide an indication of possible contamination by aromatic compounds.

15. The method of claim 1 for testing an earth sample, wherein:

said step of measuring at least one property of said extract phase comprises subjecting said extract phase to a number of narrow and discrete bands of ultraviolet radiation that each span a range of wavelengths that is narrower than about 5 nanometers, wherein said number is from 1 to 10.

16. The method of claim 1 for testing an earth sample, wherein:

the method further comprises sampling a vapor space located adjacent to and in fluid communication with said earth sample for the presence of organic vapors to provide an indication of the possible contamination of said earth sample by volatile organic components.

17. The method of claim 1, wherein:

said solvent is capable of dissolving a polyaromatic compound associated with at least one of diesel fuel, fuel oil, kerosine, creosote, coal oil, tar and asphalt.

18. The method of claim 1, wherein:

said solvent is capable of dissolving both of said organic contaminant and water.

19. The method of claim 1 for testing an earth sample, wherein:

said step of measuring at least one property of said extract phase comprises subjecting said extract phase to ultraviolet radiation in a single narrow and discrete band that spans a range of wavelengths that is narrower than about 5 nanometers.

20. The method of claim 19 for testing an earth sample, wherein:

said step of measuring further comprises determining the ability of said extract phase to absorb ultraviolet radiation in said single narrow and discrete band.

21. The method of claim 1, wherein:

said solvent comprises a $C_1$ to $C_5$ alcohol.

22. The method of claim 21, wherein:

said earth sample comprises water and humic material that is capable of being extracted, during said step of extracting, into said extract phase along with said water;

said additive is contacted, during said step of treating, with said earth sample prior to said step of extracting;

said additive ties up water of said earth sample and prevents said water from being extracted into said extract phase, whereby said humic material is also prevented from being extracted into said extract phase where it could provide a false positive indication of contamination during said step of measuring.

* * * * *